US010391038B2

(12) United States Patent
Prencipe et al.

(10) Patent No.: US 10,391,038 B2
(45) Date of Patent: Aug. 27, 2019

(54) TOOTH SEALANT

(75) Inventors: Michael Prencipe, Princeton Junction, NJ (US); Richard Scott Robinson, Belle Mead, NJ (US); Rajnish Kohli, Hillsborough, NJ (US); Richard J. Sullivan, Atlantic Highlands, NJ (US)

(73) Assignee: Colgate-Palmolive Company, New York, NY (US)

( * ) Notice: Subject to any disclaimer, the term of this patent is extended or adjusted under 35 U.S.C. 154(b) by 1382 days.

(21) Appl. No.: 12/866,766

(22) PCT Filed: Feb. 6, 2009

(86) PCT No.: PCT/US2009/033312
§ 371 (c)(1),
(2), (4) Date: Aug. 9, 2010

(87) PCT Pub. No.: WO2009/100283
PCT Pub. Date: Aug. 13, 2009

(65) Prior Publication Data
US 2010/0316726 A1    Dec. 16, 2010

Related U.S. Application Data

(60) Provisional application No. 61/027,425, filed on Feb. 8, 2008.

(51) Int. Cl.
| A61K 6/00 | (2006.01) |
| A61K 8/21 | (2006.01) |
| A61K 8/00 | (2006.01) |
| A61K 8/02 | (2006.01) |
| A61K 8/44 | (2006.01) |
| A61Q 11/00 | (2006.01) |
| A61Q 11/02 | (2006.01) |

(52) U.S. Cl.
CPC .......... *A61K 6/0017* (2013.01); *A61K 8/0216* (2013.01); *A61K 8/21* (2013.01); *A61K 8/44* (2013.01); *A61Q 11/00* (2013.01); *A61Q 11/02* (2013.01); *A61K 2800/222* (2013.01); *A61K 2800/412* (2013.01)

(58) Field of Classification Search
CPC ...... A61K 6/0017; A61K 8/0216; A61K 8/21; A61K 8/44; A61K 2800/222; A61K 2800/412; A61Q 11/00; A61Q 11/02
USPC .......................................................... 424/53
See application file for complete search history.

(56) References Cited

U.S. PATENT DOCUMENTS

| 3,925,543 A | 12/1975 | Donohue |
| 3,932,605 A | 1/1976 | Vit |
| 3,932,608 A | 1/1976 | Anderson et al. |
| 3,943,241 A | 3/1976 | Anderson et al. |
| 3,954,457 A * | 5/1976 | Weikel .......................... 420/502 |
| 3,988,434 A | 10/1976 | Schole et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,146,607 A | 3/1979 | Ritchey |
| 4,154,717 A | 5/1979 | Kohmura et al. |
| 4,154,813 A | 5/1979 | Kleinberg |
| 4,160,821 A | 7/1979 | Sipos |
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| RE31,181 E | 3/1983 | Kleinberg |
| 4,466,954 A | 8/1984 | Ichikawa et al. |
| 4,477,429 A | 10/1984 | Silbering et al. |
| 4,499,067 A | 2/1985 | Silbering et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakashima et al. |
| 4,656,031 A | 4/1987 | Lane et al. |
| 4,725,576 A | 2/1988 | Pollock et al. |
| 4,885,155 A | 12/1989 | Parran, Jr. et al. |
| 4,997,640 A | 3/1991 | Bird et al. |
| 5,096,700 A | 3/1992 | Seibel et al. |
| 5,174,989 A | 12/1992 | Tanaka et al. |
| 5,286,480 A | 2/1994 | Boggs et al. |

(Continued)

FOREIGN PATENT DOCUMENTS

| EP | 0507177 | 12/1995 |
| GB | 2354441 | 3/2001 |

(Continued)

OTHER PUBLICATIONS

US 5,989,525 A, 11/1999, Kleinberg et al. (withdrawn)
Machado et al. CaviStat Confection Inhibition of Caries in Posterior Teeth, Abstract, 83rd Session of the American Association for Dental Research, Mar. 21-24, 2007, New Orleans, LA.
Chatterjee et al,. Bacterial Acidification and CaviStat Alkalinization of Occlusal Fissure pH, Abstract, 83rd Session of the American Association for Dental Research, Mar. 9-12, 2005, Baltimore, MD.
Kleinberg I., A Mixed-Bacteria Ecological Approach to Understanding the Role of the Oral Bacteria in Dental Caries Causation: An Alternative to Streptococcus Mutans and the Specific-Plaque Hypothesis, Crit. Rev. Oral Biol. Med,. 12(2): 108-125 (2002).

(Continued)

*Primary Examiner* — Adam C Milligan

(57) ABSTRACT

The invention provides a method of treating sensitive teeth comprising attaching a sealant composition comprising a basic amino acid to a person's tooth and allowing the basic amino acid to be slowly released over time in order to reduce chrome and/or acute tooth sensitivity together with compositions and methods of use.

18 Claims, No Drawings

(56) References Cited

U.S. PATENT DOCUMENTS

| | | | |
|---|---|---|---|
| 5,334,617 | A | 2/1994 | Ulrich et al. |
| 5,369,142 | A | 11/1994 | Culbertson et al. |
| 5,370,865 | A | 12/1994 | Yamagishi et al. |
| 5,403,577 | A | 4/1995 | Friedman |
| 5,505,933 | A * | 4/1996 | Norfleet et al. ............ 424/52 |
| 5,639,795 | A | 6/1997 | Friedman et al. |
| 5,747,004 | A | 5/1998 | Giani et al. |
| 5,747,005 | A | 5/1998 | Barels et al. |
| 5,762,911 | A | 6/1998 | Kleinberg et al. |
| 5,824,720 | A * | 10/1998 | Nowak et al. ............ 523/116 |
| 5,895,788 | A * | 4/1999 | Wideman et al. ........ 514/565 |
| 5,906,811 | A | 5/1999 | Hersh |
| 5,922,346 | A | 7/1999 | Hersh |
| 5,997,301 | A | 12/1999 | Linden |
| 6,036,944 | A | 3/2000 | Winston et al. |
| 6,166,102 | A | 12/2000 | Ahn et al. |
| 6,217,851 | B1 | 4/2001 | Kleinberg et al. |
| 6,436,370 | B1 | 8/2002 | Kleinberg et al. |
| 6,488,961 | B1 | 12/2002 | Robinson et al. |
| 6,524,558 | B2 | 2/2003 | Kleinberg et al. |
| 6,558,654 | B2 | 5/2003 | McLaughlin |
| 6,616,933 | B1 | 9/2003 | Breton et al. |
| 6,805,883 | B2 | 10/2004 | Chevaus et al. |
| 7,118,376 | B2 | 10/2006 | Jodaikin et al. |
| 7,323,160 | B2 | 1/2008 | Algar et al. |
| 8,900,558 | B2 | 12/2014 | Joziak et al. |
| 2002/0081360 | A1 | 6/2002 | Burgard et al. |
| 2005/0175552 | A1 | 8/2005 | Hoic et al. |
| 2005/0266380 | A1 | 12/2005 | Soler et al. |
| 2007/0154863 | A1 | 7/2007 | Cai et al. |
| 2007/0238808 | A1 | 10/2007 | Goldberg et al. |
| 2007/0286820 | A1 | 12/2007 | Prencipe et al. |
| 2009/0068123 | A1 * | 3/2009 | Takei ............ A61K 6/083 424/52 |

FOREIGN PATENT DOCUMENTS

| | | | |
|---|---|---|---|
| JP | S57-099513 | 6/1982 | |
| JP | H02-134306 | 5/1990 | |
| JP | 7258053 | 10/1995 | |
| JP | 2000-044422 | 2/2000 | |
| JP | 2002-097125 | 4/2002 | |
| JP | 2005015435 | 1/2005 | |
| RU | 2238078 | 10/2004 | |
| WO | WO 88/001859 | 3/1988 | |
| WO | WO0078270 | 12/2000 | |
| WO | WO 2006/106838 | * 12/2006 | ............ A61K 6/00 |
| WO | WO2009100267 | 8/2009 | |

OTHER PUBLICATIONS

Kleinberg I., A New Salvia-Based Anticaries Composition, Dentistry Today, vol. 18, No. 2, Feb. 1999.

Acevedo et al., "The Inhibitory effect of an arginine bicarbonate/calcium carbonate (CaviStat)-containing dentifrice on the develpoment of dental caries in Venezuelean school children", The Journal of clinical Dentistry, 2005, v.16, No. 3,pp. 63-70, ISSN 0895-8831.

Castillo et al., 2001, "Evaluation of fluoride release from commercially available fluoride varnishes," J. Amer. Dental Assoc. 132(10):1389-1392.

Huang Yu-yuan, Liu Han-gan, eds., et al., 2008. "VI Medicinal Adhesive Materials," *Adhesive Formulations* pp. 383-384.

International Search Report and Written Opinion in International Application No. PCT/US2009/033312, dated Sep. 21, 2009.

Mashkovsky, 2001, "Drugs," Phyisician Guidance 14th ed., 2:159.

Packaging with ingredient list for DenClude® (launched Dec. 2004).

Packaging with ingredient list for ProClude® (launched Jul. 2002).

* cited by examiner

TOOTH SEALANT

This application claims the benefit of U.S. Ser. No. 61/027,425 filed Feb. 8, 2008, the contents of which are incorporated herein by reference.

FIELD OF THE INVENTION

The present invention relates to tooth sealant compositions comprising a basic amino acid in free or salt form that may be used to help prevent demineralization of teeth, alleviate pain and/or sensitivity of a patient's teeth, and provide other benefits. Sealants may include polymeric coatings, varnishes and foams to coat the teeth and/or dental device for extended periods.

BACKGROUND

Dental caries consist of demineralization of a tooth caused by bacteria. In the early stages of caries a white spot develops on the tooth and if the disease is not halted and reversed, the enamel surface breaks down to form a lesion. This can then lead to decay and eventually, a fractured tooth. It is well known that development of dental caries may be reduced by means of various factors, such as diet and oral hygiene measures, anti-microbial treatments and the provision of fluoride to the teeth.

Tooth sensitivity is also a common problem affecting children and adults. Generally, tooth sensitivity may be caused by gingival recession, dentine exposure due to erosion or abrasion, or periodontal surgery that includes root planning. Such conditions leave the dentinal tubules of the tissue susceptible to irritation by chemical, bacterial, mechanical or thermal stimuli. Examples of stimuli include heat, cold, and sweet foods. It is believed that tooth sensitivity is the result of nerve endings of the dental pulp being excited by fluid flow through the exposed dentinal tubules.

Treatments directed to alleviating pain associated with sensitive teeth have generally focused on blocking access to the dentinal tubules so as to prevent stimuli from causing pain and sensitivity. Many treatments have been developed which include application of inorganic or organic components designed to plug or otherwise block dentinal tubules for a limited time. A disadvantage of such treatments is that normal habits such as eating certain foods (e.g., foods with a high acid content) or brushing can negate the treatment. Recently, testing has revealed that increased fluoride levels within the mouth may also be used as a treatment for tooth sensitivity Toumba and Andreadis).

Current methods for administering fluoride for caries prevention include the fluoridation of drinking water, the ingestion of fluoride tablets, the incorporation of fluoride into mouth washes, toothpastes, and foods, the topical application of fluoride solutions, gels and varnishes and recently, the incorporation of fluoride in dental materials and devices.

Evidence supports the concept of frequent applications of relatively low concentrations of fluoride ions for the prevention of caries and the treatment of sensitive teeth. A sustained and controlled release delivery system could help to achieve this goal.

Arginine and other basic amino acids have been proposed for use in oral care and are believed to have significant benefits in combating cavity formation and tooth sensitivity. Combining these basic amino acids with minerals having oral care benefits, e.g., fluoride and calcium, to form an oral care product having acceptable long term stability, however, has proven challenging. Partly because of unaddressed formulation hurdles and partly because arginine has generally been viewed in the art as a potential alternative to fluoride rather than a co-active, there has been little motivation to make oral care products comprising both arginine and fluoride. Additional hurdles are potentially posed by addition of an antimicrobial agent. Commercially available arginine-based toothpaste, such as ProClude® and DenClude®, for example, contain arginine bicarbonate and calcium carbonate, but not fluoride nor any antimicrobial agent.

BRIEF SUMMARY OF THE INVENTION

In one embodiment, the invention provides a dental sealant composition comprising a basic amino acid in free or salt form (BAA). The sealant composition additionally may comprise fluoride. The BAA is preferably arginine, in free or orally acceptable salt form.

In another embodiment, the present invention relates to a method of treating sensitive teeth with a basic amino acid in free or salt form (BAA) in a sealant composition, preferably in the presence of fluoride. The method involves: (1) attaching a BAA-releasing sealant composition to a person's tooth; and (2) allowing a BAA to be slowly released over time in order to reduce chronic and/or acute tooth sensitivity. Preferably, the sealant acts also as a fluoride releasing composition as well. Because the method relies on release of a BAA into the oral cavity, the method also prevents future pain associated with dental caries by preventing demineralization and maintaining strong enamel.

The invention further provides methods to improve oral health comprising use of a dental sealant composition comprising a BAA. e.g., by a subject in need thereof, to
  a. reduce or inhibit formation of dental caries,
  b. reduce, repair or inhibit early enamel lesions,
  c. reduce or inhibit demineralization and promote remineralization of the teeth,
  d. reduce hypersensitivity of the teeth,
  e. reduce or inhibit gingivitis,
  f. promote healing of sores or cuts in the mouth,
  g. reduce levels of acid producing bacteria,
  h. to increase relative levels of arginolytic bacteria,
  i. inhibit microbial biofilm formation in the oral cavity,
  j. raise and/or maintain plaque pH at levels of at least pH 5.5 following sugar challenge,
  k. reduce plaque accumulation,
  l. treat dry mouth,
  m. whiten teeth,
  n. enhance systemic health, including cardiovascular health, e.g., by reducing potential for systemic infection via the oral tissues,
  o. reduce erosion of the teeth,
  p. immunize the teeth against cariogenic bacteria, and/or
  q. clean the teeth and oral cavity.

The invention further provides the use of a BAA in the manufacture of a dental sealant, e.g., for use in a method of treating sensitive teeth, or in any of the methods set forth above.

The sealant compositions may be used for alleviating pain and/or sensitivity of teeth in addition to any effect that the BAA releasing sealant compositions may have in preventing dental caries. The compositions may be attached to a tooth to provide slow-BAA releasing devices for releasing a BAA into the saliva of an individual.

The daily dissolution rate (DDR) of the composition under conditions in the mouth may range from about 0.1 to about 100% per day. The required DDR of the sealant composition will depend upon the duration of BAA release required. For example, if the composition is required to release a BAA over a long period, such as 1-2 years, the DDR is preferably about 0.1 to about 0.5%. However, if a BAA need only be released for a shorter period, such as a few hours, days, weeks, or months, a faster releasing sealant may be used, for example having a DDR of up to about 100%.

By "dental sealant composition" is meant a composition which attaches to the teeth. The compositions may be applied as a spray, for example using a hydrocarbon propellant. Alternatively, the compositions comprise a polymer or varnish suitable for painting onto teeth, Alternatively, the compositions may be incorporated into dental cement or filling materials. For example, the compositions may be attached to a tooth, for example being attached to rear molar using standard dental cement or as a powder for adding to dental materials, such as dental amalgams, thereby providing means to supplement a BAA release into saliva to assist in the prevention or reduction of dental caries. The powder may be included in a number of other dental materials, such as fissure sealant resins or composite bonding materials to cement bonds and brackets in orthodontic appliances. Powder applications may use sealant compositions that have a lower DDR than those that are attached directly to a tooth, for example having a DDR of about 0.1 to about 1%.

These and other benefits, advantages and features of the present invention will become more full apparent from the following description and appended claims, or may be learned by the practice of the invention as set forth hereinafter.

DETAILED DESCRIPTION OF THE PREFERRED EMBODIMENTS

The inventive method involves attaching a BAA releasing sealant composition to a person's tooth, or a dental appliance, such as a denture, and then allowing a BAA to be slowly released over time in order to reduce chronic and/or acute tooth sensitivity. According to a preferred embodiment, the BAA releasing sealant composition comprises about 5 to about 75 weight percent BAA and about 5 to about 30 weight percent fluorine.

Slow-release BAA devices consistently raise intra-oral salivary BAA levels for periods up to 2 years or more, and now also appear to completely alleviate the symptoms of dentine sensitivity within two weeks, while maintaining the benefit for up to six months or more in adults. Subjects report complete alleviation of their dentine sensitivity. There are no adverse events reported or observed. There is a slight tendency for an increase in plaque and gingival indices, but this is non-significant.

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, 1-arginine, or a salt thereof, for example arginine bicarbonate, arginine phosphate, or arginine hydrochloride.

The compositions of the invention are intended for consumption and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

The concentration of BAA will vary depending on the formulation. In one embodiment, the BAA (amount of salt expressed as weight of the free base is 1-40% by weight of the formulation, e.g. 5-20%, for example about 10%.

The compositions of the invention may additionally comprise fluoride. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In a particular embodiment, the fluoride source is sodium fluoride or sodium monofluorophosphate. The fluoride may be present in the formulation in effective amounts, as used in conventional dental sealants, e.g. higher than typically used in toothpaste. It may, for example be present, e.g., in an amount of about 2,500 ppm to about 250,000 ppm, expressed as level of fluoride ion, or in an amount of 2-25%, for example, at least 12%, e.g., 15-25% by weight of the composition.

The compositions may additionally comprise an antibacterial agent, such as triclosan, or an agent which inhibits attachment of bacteria.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the an, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Formulations comprising 10 wt % arginine bicarbonate are prepared as follows:

TABLE 1

| Ingredient | % |
|---|---|
| (Part 1) | |
| Water | QS |
| Sodium Fluoride | 2.65 |
| Malic Acid | 1.75 |
| Sodium Mono phosphate | 1.38 |
| Sodium Methyl Cocoyl Taurate | 1 |
| Flavor | 0.6 |
| Sodium Saccharin | 0.35 |
| Sodium Benzoate | 0.1 |
| Arginine Bicarbonate | 10 |
| Total (Part 1) | 100 |
| Part 2 | |
| Part 1 | 93 |
| Hydrocarbon propellant mixture | 7 |
| Total | 100 |

Example 2

Varnish formulation comprising 10 wt % arginine hydrochloride is prepared as follows:

TABLE 2

| Ingredient | % |
|---|---|
| Colophonium | 22.01 |
| 90% Ethyl Alcohol | 27.87 |
| Shellac | 21.5 |
| Mastic | 11.82 |
| Sodium Fluoride | 4.98 |
| Sodium Saccharin | 0.68 |
| Raspberry Flavor | 0.65 |
| White Beeswax | 0.48 |
| Arginine Hydrochloride | 10 |
| Total | 100 |

The invention claimed is:

1. A dental sealant composition comprising a basic amino acid in free or salt form (BAA) and fluoride ion source, wherein said fluoride ion source is present at a concentration of at least 12%, by weight, of the composition and is selected from stannous fluoride, sodium monofluorophosphate, sodium fluorosilicate, ammonium fluorosilicate, amine fluoride, aluminum fluoride, sodium hydrogen fluoride, sodium fluoride, calcium fluoride, magnesium fluoride, and potassium fluoride, wherein the composition is adapted for incorporation into a dental material and said dental material is selected from the group consisting of a dental amalgam, a fissure sealant resin, a composite bonding material, an orthodontic appliance, a dental prosthetic, a resin varnish, and an oral surgery implant, and
wherein the composition has a daily dissolution rate of from about 0.1 to about 0.5%.

2. The sealant composition of claim 1 wherein the BAA comprises arginine, in free or salt form.

3. The sealant composition of claim 1, wherein the composition is provided in powder form.

4. The sealant of claim 1, further comprising a potassium ion source.

5. The sealant of claim 4, wherein said potassium ion source is selected from potassium nitrate and potassium chloride.

6. A method of treating sensitive teeth comprising:
attaching the sealant composition of claim 1 to a tooth of a person in need thereof; and
allowing the BAA to be slowly released over time in order to reduce chronic and/or acute tooth sensitivity.

7. The method of claim 6, wherein said fluoride ion source is slowly released over time.

8. The method of claim 6, wherein the fluoride ion source is present at a concentration of about 15 to about 25 percent, by weight, of the composition.

9. The method of claim 6, wherein the composition is provided in powder form.

10. The method of claim 9, wherein the powder form comprises powder grains having a grain size of less than about 38 microns.

11. The method of claim 9, wherein the powder form comprises powder grains having a grain size of less than about 106 microns.

12. The method of claim 9, wherein the powdered form is incorporated in one or more dental materials.

13. The method of claim 6, wherein the composition comprises at least one pellet adapted for attachment to a tooth using dental cement, wherein said pellet comprises BAA.

14. The method of claim 6, wherein the sealant composition further comprises a potassium ion source.

15. The method of claim 14, wherein said potassium ion source is selected from potassium nitrate and potassium chloride.

16. A method for promoting systemic health comprising:
attaching the sealant composition of claim 1 to a tooth of a person in need thereof; and
allowing the BAA to be slowly released over time.

17. The method of claim 16, wherein the sealant composition further comprises a potassium ion source.

18. The method of claim 17, wherein said potassium ion source is selected from potassium nitrate and potassium chloride.

* * * * *